| United States Patent [19] | [11] Patent Number: 4,734,286 |
| --- | --- |
| Mahieu et al. | [45] Date of Patent: Mar. 29, 1988 |

[54] CROSSLINKED POLY β-ALANINE AND COMPOSITIONS CONTAINING THE SAME

[75] Inventors: Claude Mahieu, Paris; Christos Papantoniou, Montmorency, both of France

[73] Assignee: L'Oreal, Paris, France

[21] Appl. No.: 863,845

[22] Filed: May 16, 1986

Related U.S. Application Data

[63] Continuation of Ser. No. 513,284, Jul. 13, 1983, abandoned.

[30] Foreign Application Priority Data

Jul. 13, 1982 [LU] Luxembourg .............................. 84268

[51] Int. Cl.$^4$ .......................... A61K 9/16; C08F 8/28; C08F 20/56
[52] U.S. Cl. ..................................... 424/489; 424/501; 428/402; 514/616; 514/952; 522/152; 525/154

[58] Field of Search ................ 424/501, 489; 428/402; 521/64

[56] References Cited

U.S. PATENT DOCUMENTS

| 2,967,137 | 1/1961 | Lawton | 522/164 |
| 3,607,622 | 9/1971 | Espy | 525/427 |
| 3,728,214 | 4/1973 | Espy | 525/157 |
| 4,035,229 | 7/1977 | Rave | 162/164.3 |
| 4,079,043 | 3/1978 | Rave | 525/154 |
| 4,160,754 | 7/1979 | Schapel | 523/102 |

*Primary Examiner*—John C. Bleutge
*Assistant Examiner*—A. H. Koeckert
*Attorney, Agent, or Firm*—Cushman, Darby & Cushman

[57] ABSTRACT

A water insoluble crosslinked poly β-alanine is prepared by crosslinking poly β-alanine with a crosslinking agent selected from the group consisting of formaldehyde and a dialdehyde or by irradiation of said poly β-alanine with $Co^{60}$.

4 Claims, No Drawings

CROSSLINKED POLY β-ALANINE AND COMPOSITIONS CONTAINING THE SAME

This is a continuation of application Ser. No. 513,284, filed July 13, 1983, now abandoned.

The present invention relates to new water insoluble poly β-alanine type crosslinked polymers and to their use in various industrial fields.

More particularly the present invention relates to water insoluble crosslinked poly β-alanine.

Non-crosslinked poly β-alanine which is employed as the initial reactant in accordance with the present invention is a water soluble polymer obtained by anionic polymerization of acrylamide, the said polymer having a molecular weight generally between 500 and 200,000 with the molecular weight being determined by the light diffusion method.

Crosslinking of poly β-alanine, using various crosslinking agents, provides polymers which are insoluble in water and in conventional solvents for poly β-alanine. These crosslinked polymers exhibit novel properties which permit their successful use in many different industrial areas.

The present invention thus relates to water insoluble crosslinked poly β-alanine which is obtained by crosslinking poly β-alanine having the formula

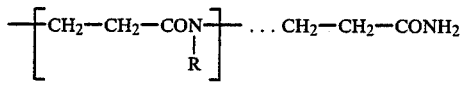

wherein
R represents hydrogen or a branching of the formula,

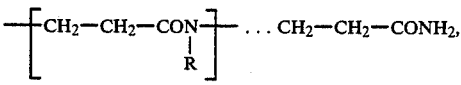

the percentage of the terminal primary amide units (b) being between 5 and 35% relative to the total amide units of the polymer,
with a crosslinking agent selected from the group consisting of formaldehyde and dialdehydes, such as glutaraldehyde, or even by irradiation with $Co^{60}$.

Poly β-alanine is a known polymer the preparation of which has been described in U.S. Pat. Nos. 2,749,331 and 4,082,730.

Its preparation consists in an anionic polymerization reaction of acrylamide in an organic solvent in the presence of a base, as an initiator.

As shown by the general formula of poly β-alanine, given above, the structure of this polymer is not only linear but it can also be branched which explains the relatively significant number of terminal primary amide units, the number of which can be regulated as a function of the polymerization process employed.

For example, the initiation of the anionic polymerization of acrylamide by sodium tert. butylate can lead to a poly β-alanine whose terminal primary amide units represent about 17 percent of the total of the amide groups of the polymer whereas initiation with sodium methylate can lead to a poly β-alanine whose terminal primary amide units represent 30 percent of the total of the amide groups of the polymer.

The basic initiator is generally used in an amount of about 0.1 to about 2 mole percent relative to the acrylamide, and the polymerization reaction is preferably carried out at a temperature in the order of 40° to about 140° C. and preferably from 60° to about 130° C.

Crosslinking of poly β-alanine can be effected according to two different methods, i.e. using certain crosslinking agents, such as formaldehyde and certain dialdehydes, in particular glutaraldehyde, or by irradiation with $Co^{60}$.

When the crosslinking is effected using a crosslinking agent, such as glutaraldehyde, so as to obtain spheres, the reaction is generally carried out in a suspension of an aqueous solution of poly β-alanine in an organic solvent, such as cyclohexane, toluene, methyl benzoate, benzyl benzoate, chlorobenzene or dichloroethane, in the presence of a suspension agent, such as a cellulose derivative, including in particular, ethyl cellulose, ethyl-hydroxyethyl cellulose and hydroxyethyl cellulose, vinyl polyacetate, maleic anhydride-octadecene copolymer, maleic anhydride-octadecyl vinyl ether copolymer, sorbitan oleates and the condensation product of ethylene oxide and propylene oxide, known under the tradenames of "Pluronics".

The suspension agent, such as defined above, has for an essential object to orient the formation of crosslinked poly β-alanine in the form of spheres whose diameter is a function of the nature and the amount of the suspension agent employed.

Thus, there can be employed, as the suspension agent, vinyl polyacetate, whereby the spheres of crosslinked poly β-alanine generally have a diameter greater than those obtained when there is used, as the suspension agent, "Pluronic 84" or hydroxyethyl cellulose.

The amount of suspension agent also plays a significant role in the production of spheres of the desired diameter. This amount can vary to a significant degree, but it is generally between 0.1 and 5 weight percent.

The amount of crosslinking agent, such as defined above, can also vary in large proportions, but is generally between 1 and 20 percent by weight relative to the weight of the poly β-alanine being reacted.

The crosslinking reaction is conducted at a temperature between 20° and 80° C. and at an acid pH, preferably between 1 and 2, which is obtained by the addition of a mineral acid, preferably hydrochloric acid.

After agitation at ambient temperature, the reaction mixture is heated to a temperature between 40° and 100° C. for a time which can vary between 1 and 6 hours.

The resulting spheres are then separated, washed initially with an organic solvent or an alcohol/soda mixture and then with water and optionally with ethanol, and finally oven dried.

As a function of the nature and amount of the suspension agent employed, the diameter of the spheres of crosslinked poly β-alanine can vary between 2 and 500 microns.

The spheres can thus be submitted to a screening operation so as to separate those whose diameter is above or below a desired certain size, for example, those outside the range of 100 to 200μ.

The above described process is more particularly employed in the production of spheres and constitutes a preferred embodiment of carrying out the present invention.

When it is desired to obtain films having a variable thickness, generally between 50µ and 3 mm, the process comprises preparing a solution in water of poly β-alanine to which is added the requisite amount of crosslinking agent, adjusting the pH of the solution to an acid pH, for example by adding hydrochloric acid, then pouring the resulting solution between two glass plates, the spacing therebetween having been previously regulated. The entire assembly is then oven dried at a temperature between 40° and 100° C., for a time which can vary between 1 and 6 hours.

After opening the mold which is constituted by the two glass plates, the film can then be submitted again to an oven drying operation or to ambient temperature.

When it is desired to obtain certain particular forms, the solution, such as described above, is poured into appropriate molds and the procedure as outlined above is followed.

Crosslinking of poly β-alanine by irradiation with $Co^{60}$ is generally carried out starting with a film of water-soluble poly β-alanine obtained by evaporation of a solution of poly β-alanine in a water/ethanol mixture titrating more than 50% alcohol.

After drying the film it is placed in an appropriate enclosure and then submitted to irradiation.

The resulting film is insoluble in water and conventional solvents for poly β-alanine.

When in the preparation of spheres of crosslinked poly β-alanine the crosslinking agent employed is a dialdehyde, such as for example glutaraldehyde, a certain percentage of the free aldehyde functions remain after the polymerization reaction so that a purification is required thereby diminishing the aggressiveness of the polymer which is particularly desirable when the spheres are to be employed therapeutically.

To this end, the purification reaction comprises transforming the remaining aldehyde functions into alcohol functions by submitting the spheres to a reduction reaction employing, for example, sodium borohydride or any other similar reducing agent.

The crosslinked poly β-alanine obtained in accordance with any one of the crosslinking processes described above exhibits the characteristic of swelling in water and retaining a significant amount of it.

Because of this characteristic, the crosslinked poly β-alanine of the present invention is particularly useful therapeutically.

The spheres of crosslinked poly β-alanine can, in effect, be used on infected, exuding, sores or wounds and function as an adsorption agent thereby facilitating the natural process of cicatrization.

In this type of application, the sore or wound is first cleaned by the application of water thereto and without having previously dried it, the crosslinked poly β-alanine is applied thereto in the form of a powder which is then covered with a sterile compress which is fixed using an adhesive or a bandage.

The crosslinked poly β-alanine can also serve to support certain water soluble active substances.

Thus, the crosslinked poly β-alanine spheres can be impregnated with certain cicatrizing products in an aqueous solution, which causes the spheres to swell up. The resulting product is then provided in the form of a paste which can be applied to the sore, thereby facilitating an exchange between the exudate of the sore and the solution contained in the paste.

It is also possible, according to the present invention, after the impregnation of the crosslinked poly β-alanine spheres using a water soluble active substance, to dry the spheres thereby retaining the active substance within the spheres. When the active substance is a cicatrizing agent, this form of the invention provides excellent healing of the sores by assuring better cicatrization.

The crosslinked poly β-alanine spheres can also be used as an excipient, preferably in admixture with conventional excipients for various active substances, in dispersion or solution.

In this case the spheres improve the consistency and also favor certain topical treatments.

Representative active substances which can be thus formulated include anti-inflammation agents, such as hydrocortisone or one of its derivatives, anti-fungus agents, such as the combinations of lauryl-oxypropyl β-aminobutyric acid and benzalkonium chloride, of N-butylamide of 4-chloro-2-hydroxy benzoic acid and salicylic acid, isothiazolone derivatives, such as the magnesium complex of 5-chloro-2-methyl isothiazolone or those described in French Pat. No. 80 22278, antibiotic agents, such as oxytetracycline hydrochloride, anti-acne agents, such as benzoyl peroxide, anti-purigineous agents, such as isothipendyl hydrochloride, anti-psoriatic agents, such as anthraline or its derivatives, for example those described in French Pat. Nos. 80 22454, 80 22455, 80 26550 and 81 02572, sunscreen agents such as benzylidene camphor derivatives, nail softening agents, such as urea and the like.

The crosslinked poly β-alanine can also be employed in various fields such as, for example, as a support for a chromatography column, as an alimentary packaging material, as a material for the production of contact lenses or artificial arteries.

The following non-limiting examples are given to illustrate the invention. Unless otherwise stated, all parts and percentages are by weight.

I. Examples of preparing crosslinked poly β-alanine in the form of spheres

Example A

In a 2 liter reactor, fitted with a nitrogen lead in tube, a condenser, a thermometer, a reactant introduction funnel and a helical stirrer, 600 grams of distilled cyclohexane are introduced, followed by the introduction of 3 grams of ethyl cellulose T 100, sold by Hercules. These components are then dissolved by heating under agitation and under nitrogen atmosphere.

After cooling to 25° C., the agitation speed is regulated to 1300 rpm and there are introduced under nitrogen, over a 15 minute period, an aqueous solution of poly β-alanine and glutaraldehyde obtained by dissolving 100 g of poly β-alanine in 70 cc of water, previously degassed and saturated with nitrogen, then 1 g of ascorbic acid and 30 g of a 25% aqueous solution of distilled glutaraldehyde, as well as concentrated HCl (d=1.18) so as to adjust the pH of the reaction mixture to 1.

At the end of the addition, the mixture is stirred for 10 minutes at ambient temperature and then heated at 50° C. for a period of 3½ hours. After this reaction period, the mixture is filtered on a Buchner funnel.

The resulting crosslinked poly β-alanine spheres are then submitted to a series of the following washing operations:

(i) the spheres are taken up, in suspension, in 800 g of cyclohexane for 15 minutes at solvent reflux and then filtered, (ii) the spheres are then taken up, in suspension, in 800 g of pure ethanol and then filtered, (iii) the spheres are taken up, in suspension, in 800 cc of water and then filtered. This operation is repeated 3 times until the last aqueous phase is neutral, and (iv) the spheres are then taken up, in suspension, in pure ethanol and finally filtered.

The resulting moist spheres are then dried on plates covered with filter paper for 24 hours at ambient atmosphere and finally stove-dried at 40° C. for 24 hours.

The resulting dried spheres are then sieved on a 315μ mesh sieve thereby yielding 50 g of a yellowish white powder of the desired size.

Measure of swelling:

A 10 ml cylinder is filled with 1 ml of spheres having a diameter ≦315μ in the dry state. The cylinder is then filled up to 10 ml by the addition of water; the spheres swell rapidly up to 5.7 ml (in the absence of any stirring).

Example B

In a 250 cc round bottom flask, fitted with a nitrogen lead in tube, a condenser, a thermometer, a reactant introduction funnel and a stirrer, 90 g of toluene are introduced then 1.8 g of vinyl polyacetate (Rhodopas HV2 sold by Rhone-Poulenc).

There are then added, with stirring and under a nitrogen atmosphere over a 10 minute period, an aqueous solution of poly β-alanine and glutaraldehyde obtained by dissolving 15 g of poly β-alanine in 13 cc of water, previously degassed and saturated with nitrogen and then 7.36 g of a 25% aqueous solution of distilled glutaraldehyde, as well as concentrated HCl so as to adjust the pH of the reaction mixture to 1.

At the end of the addition, the reaction mixture is stirred for 10 minutes at ambient temperature, and then heated to 80° C. for 3 hours. After this reaction period the mixture is filtered on a Buchner funnel.

The resulting spheres are treated with a 1:1 ethanol/2N NaOH solution, for 15 minutes at ambient temperature and then washed with water until the wash waters are neutral.

After washing the spheres the spheres are oven-dried at 40° C. for 24 hours.

The dried spheres are then sieved on a ≦450μ mesh sieve thereby yielding 4.5 g of a yellowish white powder of the desired size.

Example C

In a 250 cc round bottom flask, fitted with a nitrogen lead in tube, a condenser, a thermometer, a reactant introduction funnel and a stirrer, 90 g of benzyl benzoate are introduced, then 1.8 g of "Pluronic L64" sold by Marles-Kulmann-Wyandotte.

There is then added, with stirring, an aqueous solution of poly β-alanine and glutaraldehyde in the same amounts as those indicated in Example B, above.

The process is then carried out as in Example B with the exception that the heating temperature, after the addition is 50° C. rather than 80° C.

The resulting spheres are sieved on a 300μ mesh sieve thereby yielding 5 g of yellowish white powder of the desired size.

Example D

This example is identical to Example C above except that benzyl benzoate is replaced with the same amount of methyl benzoate and the 1.8 g of "Pluronic L64" are replaced with 0.3 g of "Cellosize WP 09", sold by B. P. Chemicals.

The resulting spheres are sieved on a 200μ sieve, thereby yielding 5 g of a yellowish white powder of the desired size.

II. Examples of the chemical modification of the spheres.

Example A

In a 2 liter reactor there are suspended 50 g of spheres having a diameter ≦315μ, obtained in Example IA above, in 800 ml of permutted water. The resulting suspension is cooled to 10° C. while maintaining the suspension under mild agitation.

There is then introduced a solution of 1.7 g of sodium borohydride ($NaBH_4$) in 200 ml of permutted water while maintaining the reaction mixture under a nitrogen atmosphere for 5 hours at 10° C. The reaction mixture is then filtered on a Buchner funnel and the recovered gel is suspended in 300 ml of water and neutralized to pH 7 by the addition of acetic acid (0.5 ml).

After filtering, the gel is washed 4 times with 400 ml of water for 15 minutes, then once with ethanol. The spheres are then dried on plates covered with filter paper at ambient temperature, followed by oven drying at 40° C.

The dried spheres are then seived using a 400μ mesh sieve before being packaged.

The absence of coloration in the presence of a Schiff reactant leads to the conclusion that the residual aldehyde functions have been reduced.

Example B

This Example is identical to Example IIA, above, except that the gel, rather than being washed with ethanol, is washed with 200 ml of a 0.1% solution of lauryl sulfate in triethanolamine which provides spheres of a higher quality as they do not agglomerate on drying.

III. Examples of preparing crosslinked poly β-alanine by irradiation with $Co^{60}$.

Example A

A 7×15 cm film of soluble poly β-alanine having a thickness of 0.5 mm is initially prepared by evaporation, in a vat, of a 40% solution of soluble poly β-alanine in a 50:50 water-ethanol mixture. After drying the resulting film, the latter is packaged in an enclosure at 55° relative humidity, then exposed to a total irradiation dosage of 27 MRad.

The resulting film of crosslinked poly β-alanine is insoluble in water and conventional solvents for poly β-alanine.

Example B

According to a variation of Example IIIA, above, a water-impregnated gas is inserted between two films of soluble poly β-alanine such as obtained above. After having compressed and dried the whole, the structure having the same inserted is submitted, as above, to irradiation so as to crosslink the poly β-alanine films.

IV. Examples of preparing crosslinked poly β-alanine in the form of films.

Example A

A solution containing 30 g of soluble poly β-alanine, 30 cm³ of water and 3 g of distilled glutaraldehyde is adjusted to pH 1 by the addition of the requisite amount of concentrated HCl. The resulting solution is then poured into a mold constituted by two 20×20 cm glass plates having a 0.6 mm spacing therebetween. The mold is then placed in an oven at 50° C. for 3 hours.

After opening the mold, a film of crosslinked poly β-alanine is obtained which can be dried by exposure to air at ambient temperature.

Example B

A solution containing 28.4 g of soluble poly β-alanine, 20 cm³ of water and 1 cm³ of a 40% solution of formaldehyde in water is adjusted to pH 1 by the addition of the requisite amount of concentrated HCl. The resulting solution is poured very rapidly into a mold constituted by two 20×20 cm glass plates having a 0.6 mm spacing therebetween. The mold is then left for 15 minutes at 25° C.

After opening the mold a film of crosslinked poly β-alanine is obtained which can be dried by exposure to air at ambient temperature.

V. Examples of Use

Example 1

Poly β-alanine spheres prepared in accordance with Example IIB are applied to the surface of a exuding sore and are maintained in contact therewith using a bandage.

The spheres permit acceleration of the cicatrization of the sore or wound.

Example 2

A pommade, weighing 100 g and containing 3 g of the spheres of poly β-alanine prepared according to Example IIB together with a mixture of polyethylene gylcol 400 and polyethylene glycol 1000 as an excipient, is applied on a exuding sore.

By repeating application of this pommade, the cicatrization of the sore is accelerated.

Example 3

A pommade for use in treating an exuding sore is prepared by admixing the following components:

| | |
|---|---|
| Vitamin A | 200,000 I.U. |
| Tyrothricin | 60 mg. |
| Crosslinked poly β-alanine prepared in accordance with Example IIA | 5 g. |
| Polyethylene glycol 1000, as an excipient, in an amount sufficient for | 100 g. |

On application of this pommade, the cicatrization of the sore is accelerated.

Example 4

5 g of crosslinked poly β-alanine, in the form of spheres, obtained in accordance with Example IIB, are contacted with 50 g of water containing 1 g of histidine. The poly β-alanine spheres swell up very rapidly and take the form of a gel. The gel is dried under reduced pressure. Thus, the poly β-alanine spheres are recovered in their initial form except that they contain histidine enclosed therein. The spheres thus charged with histidines are packaged in the form of a pommade by using, as an excipient, polyethylene glycol 400 and polyethylene glycol 1000.

Example 5

5 g of crosslinked poly β-alanine, in the form of spheres, prepared in accordance with Example IIB are contacted with 25 g of water containing 0.5 g of histidine. The spheres of swollen poly β-alanine are then packaged in the form of a pommade with polyethylene glycol 400 and polyethylene glycol 1000.

Example 6

A pommade in accordance with the present invention is prepared by admixing the following components:

| | |
|---|---|
| Neomycin sulfate | 0.35 g |
| Crosslinked poly β-alanine prepared in accordance with Example IIB | 3 g |
| Polyethylene glycol 400 and polyethylene glycol 1000, sufficient amount for | 100 g |

This pommade or ointment is usefully employed for the treatment of exuding sores and it favors cicatrization thereof.

Example 7

There is prepared in accordance with the present invention, an anti-psoriatic ointment by admixing the following components:

| | |
|---|---|
| Anthralin | 0.5 g |
| Crosslinked poly β-alanine prepared in accordance with Example IIB | 2 g |
| Silica | 8 g |
| Isopropyl myristate, sufficient amount for | 100 g |

Example 8

An anti-acne ointment is prepared by admixing the following components:

| | |
|---|---|
| Benzoyl peroxide | 5 g |
| Crosslinked poly β-alanine | 15 g |
| Triglycerides of capric, caprylic and stearic acids | 40 g |
| Beeswax | 10 g |
| Petrolatum | 20 g |
| Triglycerides of capric and caprylic acids, in an amount sufficient for | 100 g |

In this example the benzoyl peroxide can optionally be combined with neomycin.

Example 9

An anti-acne ointment in accordance with present invention is prepared by admixing the following components:

| | |
|---|---|
| Glycerol stearate and sorbitan stearate | 30 g |
| Retinoic acid | 0.2 g |
| Crosslinked poly β-alanine prepared in accordance with Example IIB | 10 g |
| Petrolatum oil, sufficient amount for | 100 g |

In this Example, the retinoic acid can optionally be combined with erythromycin base and in this case one employs 4 g of erythromycin per 0.05 g of retinoic acid.

Example 10

In accordance with th present invention an antibiotic-/antifungus ointment is prepared by admixing the following components:

| | |
|---|---|
| Triamcinolone acetonide | 0.1 g |
| Neomycine sulfate | 0.25 g |
| Nystatine | 10,000,000 I.U. |
| Crosslinked poly β-alanine prepared in accordance with Example IIB | 5 g |
| Lanolin | 25 g |
| Triglycerides of capric and caprylic acids | 35 g |
| Beeswax | 15 g |
| Petrolatum, sufficient amount for | 100 g |

Example 11

In accordance with the present invention an anti-inflammation ointment is prepared by admixing the following components:

| | |
|---|---|
| Indometacine | 1 g |
| Crosslinked poly β-alanine prepared in accordance with Example IIB | 7 g |
| Polyethylene glycol 400 | 60 g |
| Polyethylene glycol 4000 | 25 g |
| Petrolatum oil, sufficient amount for | 100 g |

Example 12

In accordance with the present invention an anti-inflammation ointment is prepared by admixing the following components:

| | |
|---|---|
| 17-butyrate of hydrocortisone | 0.1 g |
| Crosslinked poly β-alanine prepared in accordance with Example IIA | 6 g |
| Sorbitan sesquioleate | 10 g |
| Isopropyl myristate | 35 g |
| Beeswax | 20 g |
| Triglycerides of capric and caprylic acids, sufficient amount for | 100 g |

Example 13

In accordance with the present invention an anti-fungus/anti-bacteria powder is prepared by admixing the following components:

| | |
|---|---|
| Tolnaftate | 0.5 g |
| Crosslinked poly β-alanine prepared in accordance with Example IIA, in an amount sufficient for | 100 g |

The preparation of this powder is obtained by mechanically mixing the active ingredient, tolnaftate, with the poly β-alanine spheres. In this Example the tolnaftate can be prepared by a mixture of tolnaftate and mystatine.

Example 14

In accordance with the present invention an anti-inflammation powder is prepared by admixing the following components:

| | |
|---|---|
| The sodium salt of indometacine | 1 g |
| Crosslinked poly β-alanine prepared in accordance with Example IIB, in an amount sufficient for | 100 g |

The preparation of this powder is made by the lyophilization of an aqueous solution containing the crosslinked poly β-alanine spheres and the indometacine.

Example 15

A dermal ointment for the treatment of eczema is prepared by admixing the following components:

| | |
|---|---|
| Hydrocortisone acetate | 1 g |
| Crosslinked poly β-alanine prepared in accordance with Example IIB | 2 g |
| Excipient - Polyethylene glycol 4000, 1500 and 300, lano-petrolatum and propylene glycol, in an amount sufficient for | 100 g |

Example 16

In accordance with the present invention a composition for the treatment of surface cutaneous mycoses is prepared by admixing the following components:

| | |
|---|---|
| Lauryl oxypropyl-β-aminobutyric acid | 2 g |
| Benzalkonium chloride | 0.5 g |
| Tartaric acid, amount sufficient for pH 3.3–3.6 | |
| Water, sufficient amount for | 100 g |

5 g of the spheres prepared in accordance with Example IIB are introduced into 25 g of the above solution. After swelling up, the spheres are packaged in the form of an ointment weighing 100 g by using a sufficient amount of polyethylene glycol 400 and 1000, as the excipient.

Example 17

An ointment for the treatment of surface cutaneous mycoses is prepared by admixing the following components:

| | |
|---|---|
| N—butyl amide of 4-chloro-2 hydroxy benzoic acid | 10 g |
| Salicylic acid | 2 g |
| Crosslinked poly β-alanine prepared in accordance with Example IIB | 5 g |
| Excipient: mixture of petrolatum, petrolatum oil and lanolin, in amount sufficient for | 100 g |

Example 18

A composition for the treatment of surface cutaneous mycoses is prepared by admixing the following components:

| | |
|---|---|
| Magnesium complex of 2-methyl-5-chloro isothiazolone | 1 g |
| Crosslinked poly β-alanine prepared in accordance with Example IIB | 2 g |

| Excipient: Mixture of polyethylene glycol 4000, 1500 and 300, lanopetrolatum and propylene glycol in an amount sufficient for | 100 g |

In this example the 2-methyl-5-chloro isothiazolone can be replaced by one of the compounds disclosed in French Pat. No. 80 22278.

Example 19

In accordance with the present invention a composition for the treatment of cutaneous infections is prepared by admixing the following components:

| Oxytetracycline hydrochloride | 450 mg. |
| Crosslinked poly β-alanine prepared in accordance with Example IIB | 1 g |
| Excipient: mixture of petrolatum and petrolatum oil in an amount sufficient for | 15 g |

Example 20

In accordance with the present invention a composition for the treatment of acne is prepared by admixing the following components:

| Benzoyl Peroxide, 100% | 5 g |
| Crosslinked polyacrylic acid, sold under the tradename "Carbopol 940" | 0.8 g |
| Colloidal silica | 0.021 g |
| Propylene glycol | 4 g |
| Copolymer of polyethylene glycol/propylene glycol | 0.02 g |
| Crosslinked poly β-alanine prepared in accordance with Example IIB | 5 g |
| 10% solution of NaOH, sufficient amount for pH 6 | |
| Water, sufficient amount for | 100 g |

Example 21

Preparation of an anti-prurigineous composition—0.75 g of isothipendyl hydrochloride is dissolved in 10 g of water. To this solution there are added 2 g of crosslinked poly β-alanine spheres, prepared in accordance with Example IIB. After the spheres swell up, the resulting gel is packaged together with, in an amount sufficient to provide 100 g of the composition, an excipient constituted by a mixture of carboxymethyl cellulose, sorbitol, sorbic acid, ethylene diamine tetraacetate and water.

Example 22

In accordance with the present invention a composition for softening the nails is prepared by admixing the following components:

| Urea | 35 g |
| Paraffin | 5 g |
| Anhydrous lanolin | 20 g |
| Petrolatum | 20 g |
| Type H silica gel | 10 g |
| Crosslinked poly β-alanine prepared in accordance with Example IIB | 10 g |

Example 23

Preparation of a sunscreen composition.

200 mg of 4-[(2-oxo-3-bornylidene)methyl] phenyl trimethyl ammonium methyl sulfate are dissolved in 50 ml of water. To this solution there are added 5 g of finely crushed crosslinked poly β-alanine spheres prepared in accordance with Example IIB. The crosslinked poly β-alanine spheres rapidly swell until the totality of this solution is absorbed. The resulting gel is then dried at 50° C. under reduced pressure and the resulting powder is dispersed in a solution composed of 48 g of petrolatum oil and 2 g of 2-ethyl hexyl 4-N,N-dimethylamino-benzoate.

Example 24

An anti-cellulitis composition is prepared by admixing the following components:

| Caffeine | 5 g |
| Ethanol (96%) | 50 ml |
| Polyacrylic acid | 1 g |
| Crosslinked poly β-alanine prepared in accordance with Example IIB | 5 g |
| Triethanolamine | 1.13 g |
| Water, sufficient amount for | 100 g |

In this example, the caffeine can be replaced by the same amount of a xanthine derivative such as that described in European Pat. No. 80-102389.

What is claimed is:

1. A cosmetic or pharmaceutical composition comprising a water-insoluble crosslinked poly β-alanine in the form of spheres having a diameter ranging from 2 to 500 microns and being prepared by crosslinking poly β-alanine having the formula

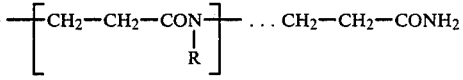

(a)   (b)

wherein R represents hydrogen or a branching of the formula,

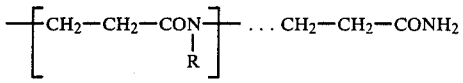

(a)   (b)

the percentage of terminal primary amide units (b) being between 5 and 35 percent relative to the total amide units of the polymer, said crosslinking being carried out with a crosslinking agent selected from the group consisting of glutaraldehyde and formaldehyde in an aqueous solution of said poly β-alanine at an acid pH.

2. The composition of claim 1 wherein said crosslinked poly β-alanine is an absorption agent for facilitating the natural process of cicatrization.

3. The composition of claim 1 wherein said crosslinked poly β-alanine is a support capable of being impregnated with a water soluble active substance.

4. The composition of claim 1 wherein said crosslinked poly β-alanine is an excipient for active substances, in dispersion or in solution.

* * * * *